US005386823A

United States Patent [19]

Chen

[11] Patent Number: 5,386,823

[45] Date of Patent: Feb. 7, 1995

[54] OPEN LOOP COOLING APPARATUS

[75] Inventor: Yasu T. Chen, San Antonio, Tex.

[73] Assignee: The United States of America as represented by the Secretary of the Air Force, Washington, D.C.

[21] Appl. No.: 907,279

[22] Filed: Jul. 1, 1992

[51] Int. Cl.[6] .......... A61M 16/00; A62B 7/00; F24F 5/00; F25D 23/12

[52] U.S. Cl. .......... 128/204.15; 128/201.24; 128/201.29; 128/205.12; 128/205.25; 62/259.3; 165/46; 2/901; 2/DIG. 1

[58] Field of Search .......... 128/201.22–201.25, 128/201.29, 202.11, 202.19, 204.15, 204.16, 204.18, 205.12, 205.18, 205.25; 2/2.1 A, 69, 81, 2.14, 2.11, 2.5, 901, DIG. 1; 62/259.3, 237, 409, 411, 412; 165/46

[56] References Cited

U.S. PATENT DOCUMENTS

| | | | |
|---|---|---|---|
| 2,413,386 | 12/1946 | Schulz | 128/201.29 |
| 3,000,191 | 9/1961 | Stark | 128/204.15 |
| 3,630,039 | 12/1971 | Hayashi | 62/5 |
| 3,744,555 | 7/1973 | Fletcher et al. | 165/46 |
| 3,869,871 | 3/1975 | Rybalko et al. | 62/178 |
| 4,024,730 | 5/1977 | Bell et al. | 62/259 |
| 4,172,454 | 10/1979 | Warncke et al. | 128/142.5 |
| 4,237,877 | 12/1980 | Boehler | 128/204.15 |
| 4,307,447 | 2/1989 | MacDonald et al. | 62/259.3 |
| 4,356,294 | 8/1989 | Scaringe et al. | 62/259.3 |
| 4,405,348 | 9/1983 | Pasternack | 62/259.3 |
| 4,545,379 | 10/1985 | Jenkins | 128/399 |
| 4,549,541 | 10/1985 | Sundahl | 128/201.24 |
| 4,591,762 | 9/1987 | Elkins et al. | 165/46 |
| 4,718,429 | 1/1988 | Smidt | 128/400 |
| 4,738,119 | 4/1988 | Zafred | 62/259.3 |
| 4,903,694 | 2/1990 | Hager | 128/204.15 |
| 4,905,475 | 3/1990 | Tuomi | 62/3.3 |
| 5,027,807 | 7/1991 | Wise et al. | 128/201.29 |

OTHER PUBLICATIONS

Hawley's Condensed Chemical Dictionary, 11th ed., Eds. Sax & Lears, Sr., Van Nostrand Reinhold Co, N.Y. 1987, ISBN 0442280971.

*Primary Examiner*—Kimberly L. Asher
*Attorney, Agent, or Firm*—Gerald B. Hollins; Thomas L. Kundert

[57] ABSTRACT

An open loop portable personnel cooling apparatus which provides cleanup of contaminated ambient air used in the cooling process is described. The described apparatus supplements rather than disables the normal cooling process of human physiology by providing a large quantity of cooling air that is moved with significant perspiration evaporation velocity within a protective clothing ensemble. The disclosed apparatus provides cooling for up to five separate protected persons with capacities and cooling capability in excess of previously known personal cooling systems. Use of the cooling system for electronic and other military equipment is also disclosed.

9 Claims, 3 Drawing Sheets

OPEN LOOP COOLING APPARATUS

RIGHTS OF THE GOVERNMENT

The invention described herein may be manufactured and used by or for the Government of the United States for all governmental purposes without the payment of any royalty.

BACKGROUND OF THE INVENTION

This invention relates to the field of personal cooling apparatus of the open loop type as may be used by workers in a heated, contaminated, or otherwise hostile environment.

As was indicated by considerable worry over possible chemical warfare in the 1991 liberation of Kuwait activities in the middle East, the difficulties associated with a chemical warfare agent and its clean-up remain of concern in the U.S. military. Although a number of existing systems and methods helpful in the performance of this effort have been available and are continuing to evolve, the extreme complexity and compounded human work difficulties attending such efforts continue to stimulate inventive solutions to certain aspects of the problem.

In my previous patent application, Ser. No. 07/548,454 Chemical Warfare Cooling System and Method there is disclosed, for example, a portable cooling apparatus of the closed circuit liquid type which is especially well adapted to extreme environmental conditions and the ultimate in chemical warfare hostility. The cooling apparatus of this prior application, which is currently under secrecy order in the U.S. Patent Office, is especially useful for relief of cleanup worker heat exposure.

The cooling apparatus of this prior patent application and several of the cooling arrangements patented by others-as are cited below herein, are found to be effective in the removing of heat from a working person. The liquid based cooling systems of these inventions, that is systems wherein cooled liquid passing through tubing or the like is brought in close proximity with the skin of a protected person, are however found to have certain significant disadvantages. A principal one of these disadvantages is concerned with the fact that such systems can actually become counter productive with respect to removing heat from a working person. More precisely, the maintenance of a cool skin condition is found to activate a blood flow restricting physiological response in the working person's body and this restricted blood flow-at the cooled skin surface, actually becomes a hindrance to the offloading of heat from the protected person's body. Such a shutdown of the body's normal heat offloading mechanism is clearly undesirable in a personal cooling apparatus.

Several examples of patent activity in the field of maintaining personal environment temperatures are identified in my previous patent application; these patents include the multiple person apparatus of U.S. Pat. No. 4,691,762 of William Elkins et al which involves quick disconnect couplings and individual control units for each person. Also included is the apparatus of U.S. Pat. No. 4,024,730 of Richard L. Bell et al where the warm-up of liquid oxygen or other breathable gas is accomplished by body heat from the cooled individual. Additionally, included in these patents are the personal cooling systems arranged to be borne by the user including the system of U.S. Pat. No. 3,869,871 of A. P.

Rybalko et al; the apparatus of U.S. Pat. No. 3,172,454 of Ernst Warncke et al; the apparatus of U.S. Pat. No. 4,405,348 of A. Pasternak; and the apparatus of U.S. Pat. No. 4,807,447 of J. R. Macdonald et al.

Of additional interest with respect to the present invention is the U.S. Pat. No. 4,856,294 of R. P. Scaringe et al which discloses a vest-like structure employing a phase changeable heat transfer material having phase transition temperatures in a selected moderate range; this close change material is also possibly supplemented by the use of ice. Additionally included is the personal comfort conditioner of Donald Tuomi in U.S. Pat. No. 4,905,475 which discloses an electrically powered heater having sources of cool and warm air which are selected by vane apparatus for delivery to the person being assisted.

Also included in this art is the U.S. Pat. No. 4,738,119 of P. R. Zafred which involves a vest-like structure cooled by sublimating carbon dioxide gas for example. The medical treatment vest-like cooling apparatus of Udo Smidt as disclosed in U.S. Pat. No. 4,718,429 wherein cooling is applied to a patient in order to stimulate body consumption of fatty deposits is also of background interest.

Further included in this patent art is the body cooling device of J. F. Jenkins as described in U.S. Pat. No. 4,545,379 which involves a seating apparatus for the user and provides a face cooling air outlet and hand cooling outlets. This patent also discloses a number of earlier body cooling apparatus patents.

Also included this art is U.S. Pat. No. 3,744,555 issued to J. C. Fletcher et al which involves a cooling garment and sensors responsive to the user's skin temperature for controlling the cooling apparatus. Additionally included is the U.S. Pat. No. 3,630,039 of T. Hayashi which discloses a compressor based personal cooling system which employs a vortex separation of air of differing temperatures.

Although each of these examples of previous work in the personal cooling art is of general interest with respect to the present inventions, none of these prior patent arrangements is fully satisfactory for the chemical warfare cleanup environment of the present invention. It is particularly notable that none of these prior personal cooling arrangements has adequately seized upon the advantages to be realized from using the moisture evaporation normal cooling mechanism of the human body in a personal cooling equipment setting. In addition none of these prior patented system is equipped with its own power source to provide power for operation.

SUMMARY OF THE INVENTION

In the present invention, there is provided a multiple person cooling apparatus in which each person being cooled is connected by a tether conduit to an open loop portable source providing large quantity cooled, dried and cleansed ambient air for use during either cleanup resting periods or work activities. The portable cooling apparatus maintains a supply of temperature regulated and contaminant-cleansed ambient air in suitable quantity and temperature for either short term or long term use by chemical warfare cleanup personnel. A significant aspect of the invention is concerned with using and enhancing the operation of the body's normal evaporation-of-water cooling mechanism in the personal cooling environment. Cool, dry and decontaminated air (at 50 to 60 degrees F for example) is circulated in sufficient quantity and with such movement velocity (e.g. 20 CFM) as to utilize and reinforce the function of the body's normal cooling mechanism. This circulation may, in fact, be characterized as providing substantial perspiration evaporation assisting predetermined pattern movement velocity over the user's body. The system of the invention is also portable and compact and can be transported by commercial or military vehicle to locations where cool air is needed, including sites where a power source is unavailable.

It is therefore an object of the present invention to provide a portable cooling apparatus usable with chemical warfare cleanup protective gear.

It is another object of the invention to provide an open loop personal cooling apparatus for use with the chemical defense warfare ensemble (CDWE) used by the U.S. military.

It is another object of the invention to provide an open loop source of cooled, dried and purified air for use by persons operating in a chemical warfare environment.

It is another object of the invention to provide a personal cooling apparatus which overcomes the disadvantages of backpack cooling systems.

It is another object of the invention to provide a personal cooling arrangement which emphasizes or reinforces the human body's heat offloading mechanism.

It is another object of the invention to provide a chemical warfare defense ensemble cooling system which uses large quantity moving dry air as a cooling medium.

It is another object of the invention to provide a personal cooling apparatus in which moving cool dry air is supplied in sufficient quantity to effectively use the body's evaporative heat rejection process even in a closed environment.

It is another object of the invention to provide a cooling arrangement in which the same treated air can be used for cooling and breathing purposes within a CDWE protective closure.

It is another object of the invention to provide an air vest inclusive chemical warfare ensemble cooling system.

It is another object of the invention to provide a personal cooling system that is usable under a variety of work and environmental conditions.

It is another object of the invention to provide a personal cooling system which may be used conveniently in a variety of hostile environments.

It is another object of the invention to provide a personal cooling system which may also be used to maintain desirable environmental conditions for electronic equipment or environmentally sensitive apparatus.

Additional objects and features of the invention will be understood from the following description and claims and the accompanying drawings.

These and other objects of the invention are achieved by the method for enabling sustained worker activity in a chemical warfare agent contaminated high temperature and high humidity ambient environment comprising the steps of:

- isolating said worker from said ambient environment in an enclosing ensemble of protective clothing;
- delivering a predetermined volume pressurized open loop flow of treated ambient air into space surrounding said worker in said protective clothing ensemble;
- treating said pressurized flow of ambient air with cooling and drying closed cycle mechanical refrigeration prior to said delivering step;
- cleansing said pressurized flow of ambient air of said chemical warfare agent contamination prior to said delivering step; a
- distributing said cooled, dried, and cleansed air with substantial perspiration evaporation assisting predetermined pattern movement velocity over predetermined body surfaces of said worker within said protective clothing ensemble.

DETAILED DESCRIPTION

Figure 1:
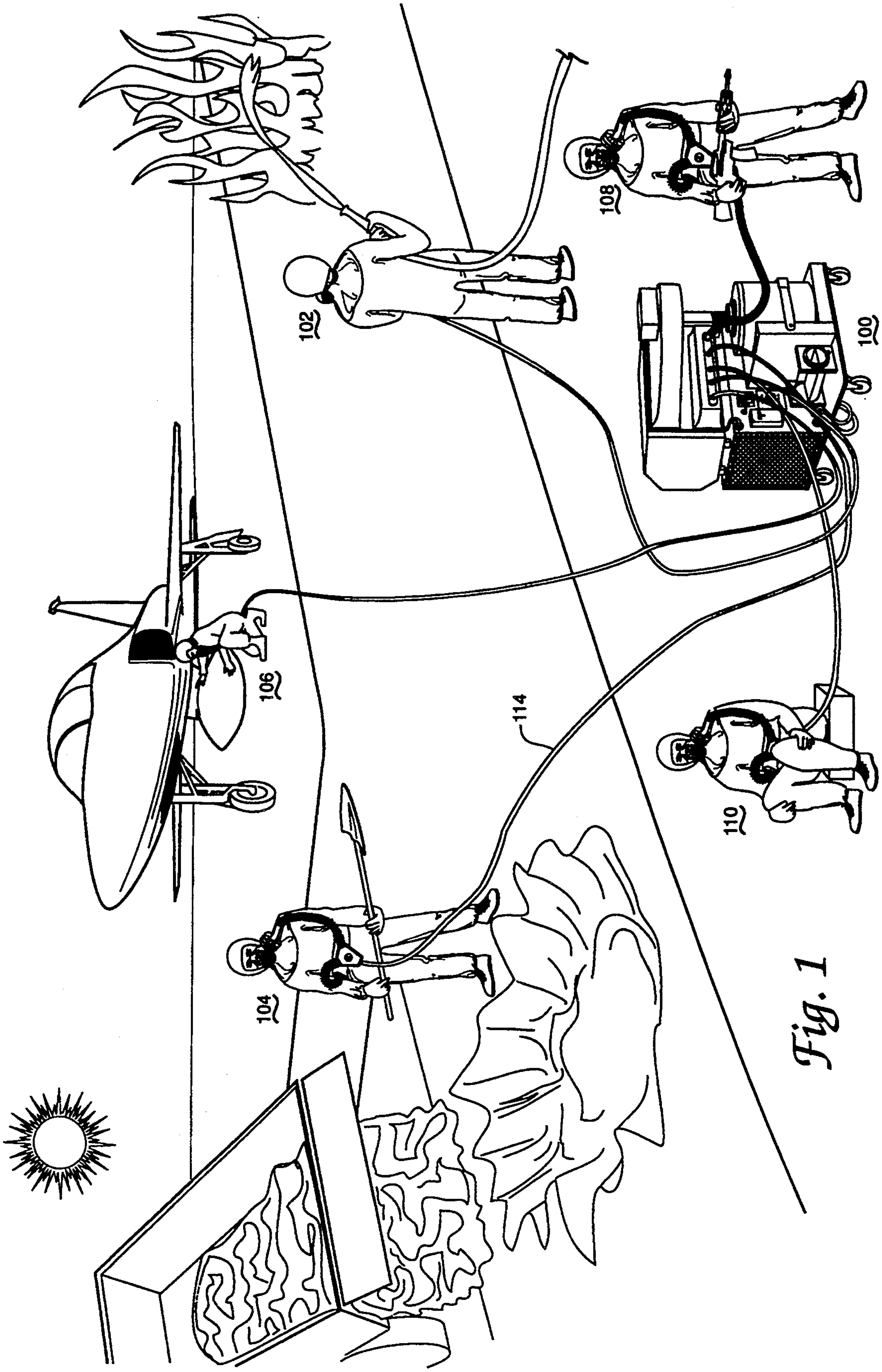
FIG. 1 shows use of apparatus according to the present invention in a representative military situation.

FIG. 1 in the drawings shows a not-to-scale representative effort as might be accomplished by Air Force personnel following an enemy action which involved combined conventional weapons and chemical/biological warfare agents. Efforts of the type shown in FIG. 1 are also to be expected following an accident sequence and the unintentional discharge of chemical/biological agents or other hazardous materials. In the FIG. 1 drawing, a plurality of workers are shown to be involved in a variety of activities including fire control equipment (or washdown) at 102, runway damage repair at 104, ordnance loading at 106, and security duty at 108.

Additionally, in the FIG. 1 drawing, the worker 110 is shown in a posture usable in the rest portion of a work and rest-cooldown cycle of activity which may also employ the present invention. Each of the FIG. 1 workers is shown to be connected by flexible tether or portable hose apparatus, shown typically at 114, to a source 100 of clean temperature regulated and pressurized coolant air. The source apparatus 100 is described in detail in the paragraphs below herein. Each of the FIG. 1 workers is also equipped with a chemical warfare Defense Warfare (CDWE) or equivalent suit of protective clothing which includes a facial protection mask having a side entry aperture for breathing/cooling air and a front opening aperture for expended facial region breathing/cooling air.

Several aspects of the FIG. 1 represented activities are significant with respect to the present invention. One of these aspects is concerned with the fact that many cleanups involving military action are of an extended and multi-person work effort nature, that is, the size and nature of the materials to be handled do not respond effectively to short-term, small-scale efforts. Another aspect of these efforts is concerned with the open air and unprotected environment for such efforts. Yet another aspect of these efforts is that a sizable percentage of the work is of such nature as to require human action rather than machine performed activity. Both the feedback of accomplished results and the variety of tasks to be performed suggest an intimate involvement of humans to provide the most effective final results.

Another aspect of these military efforts involves the possible encountering of several hazards in combination, i.e., the ordinance damage at 104 and the contamination, for example, complicates hazard remedial efforts. Another aspect of the FIG. 1 activity indicates that the work to be performed is often complicated by adverse environmental conditions, particularly the presence of tropical ambient temperatures that are extremely taxing when combined with the protective clothing necessitated by chemical warfare. The thermal discomfort often encountered when wearing rain protective clothing in the bright sunlight after a summer shower is a mild common example of the conditions to be expected during military efforts as were prepared-for during operation Desert Storm for example.

Another aspect of the FIG. 1 scene which may be appreciated with some reflection, is that contaminated protective clothing worn by a worker is removed with such difficulty and hazard to the worker and colleagues that the wearing of this clothing is preferably continued without interruption during all phases of an embarked-upon effort. Removal of the protective clothing for rest or cooldown activities is particularly impractical, and therefore suggestive of clothing which includes worker cooling arrangements.

In my above identified previous U.S. Pat. No. application of Jul. 2, 1990, activities such as are represented in FIG. 1 are enabled through the use of a closed circuit cooled liquid circulating arrangement. Here work engaged workers and workers resting between periods of activity may be connected by a two-way flow tether arrangement to a temperature regulated source of cooling liquid. In this system an ethylene glycol solution is circulated through an array of fluid conveying tubing surrounding the worker's torso and offers a helpful degree of temperature maintenance or a periodic relief cycle from excessive temperatures inside of an airtight protective garment.

Although the arrangement of this prior invention does indeed provide helpful and enabling relief for work activity in the hostile environment of a chemical or biological warfare scene, the liquid cooling system of this prior invention has been found to have several disadvantages which are overcome by the present invention. One of these disadvantages is of course concerned with the complexity and difficulty of maintaining a liquid inclusive cooling system in integral condition in the presence of work activity and difficult conditions. The propensity for liquids to escape captivity through leaks and ruptures and other unplanned events is of course, well understood.

In addition, a fundamental human physiology related consideration also mitigates against the forced cooling of skin surfaces as is accomplished with liquid based cooling apparatus. Human physiology in fact employs a plurality of cooling mechanisms in an exercising person. The most pronounced and well known of these mechanisms is through evaporation of perspiration from the skin surface. In addition to this cooling, which actually occurs by way of the large latent heat of evaporation of water, the act of perspiring is also accompanied by a dilation of the blood supplying paths adjacent the skin surface of a temperature elevated working person. It is recognized in the above cited U.S. Patent of R. P. Scaringe et al, U.S. Pat. No. 4,856,294, however that low temperature cooling of a person's skin also has undesirable effects. In fact, enforced low skin temperature opposes this dilation of blood supply passages-and actually acts to constrict these passages so that heat transfer through the skin is degraded.

To improve upon the cooling arrangement disclosed in my above referred-to prior patent application therefore, I have herein provided a personal cooling arrangement which can be used under chemical warfare protection clothing while operating on the principal of enhancing or taking advantage of these normal human physiology cooling mechanisms. That is, the present invention system takes advantage of a person's tendency to perspire and to have dilated skin area blood supply when working in a heated environment.

The mechanism for accomplishing this reliance upon normal physiology responses in the human body is of course, to provide a supply of cooled and dried clean air which is moving with a sufficient volume and velocity over the wetted skin surface of a working person as to maintain desirable temperatures within the person's body.

In practice it is found that for ambient environments above 105 degrees Fahrenheit and 95 percent relative humidity the overall results achieved with a moving air personal cooling system as disclosed in the present invention is significantly better than that achieved with non-moving air or liquid based systems. In the prior patents discussed in the background of the invention section above it is notable that a number of cooling arrangements have been base upon the circulation of liquid and forced skin temperature concepts however. Even systems recited in the identified collection of patents and operating on the cooling by gas principal have not made provision for supplying the cooling air or other gas with such volume and velocity as is capable of achieving satisfactory cooling of a working person. In particular it has been found that an average person performing moderate physical exercise in an enclosed and airtight clothing ensemble needs to be provided with removal of about 6,200 British thermal units per hour (6200 BTUH) or with an air volume of 20 cubic feet per minute when this air is held in the 50 to 60 degree Fahrenheit and 30–50 per cent relative humidity condition. The source of clean temperature regulated, and pressurized ambient air shown at 100 in the FIG. 1 cleanup scene is therefore of quantitative significance as an enabling part of the FIG. 1 activities.

Figure 2:
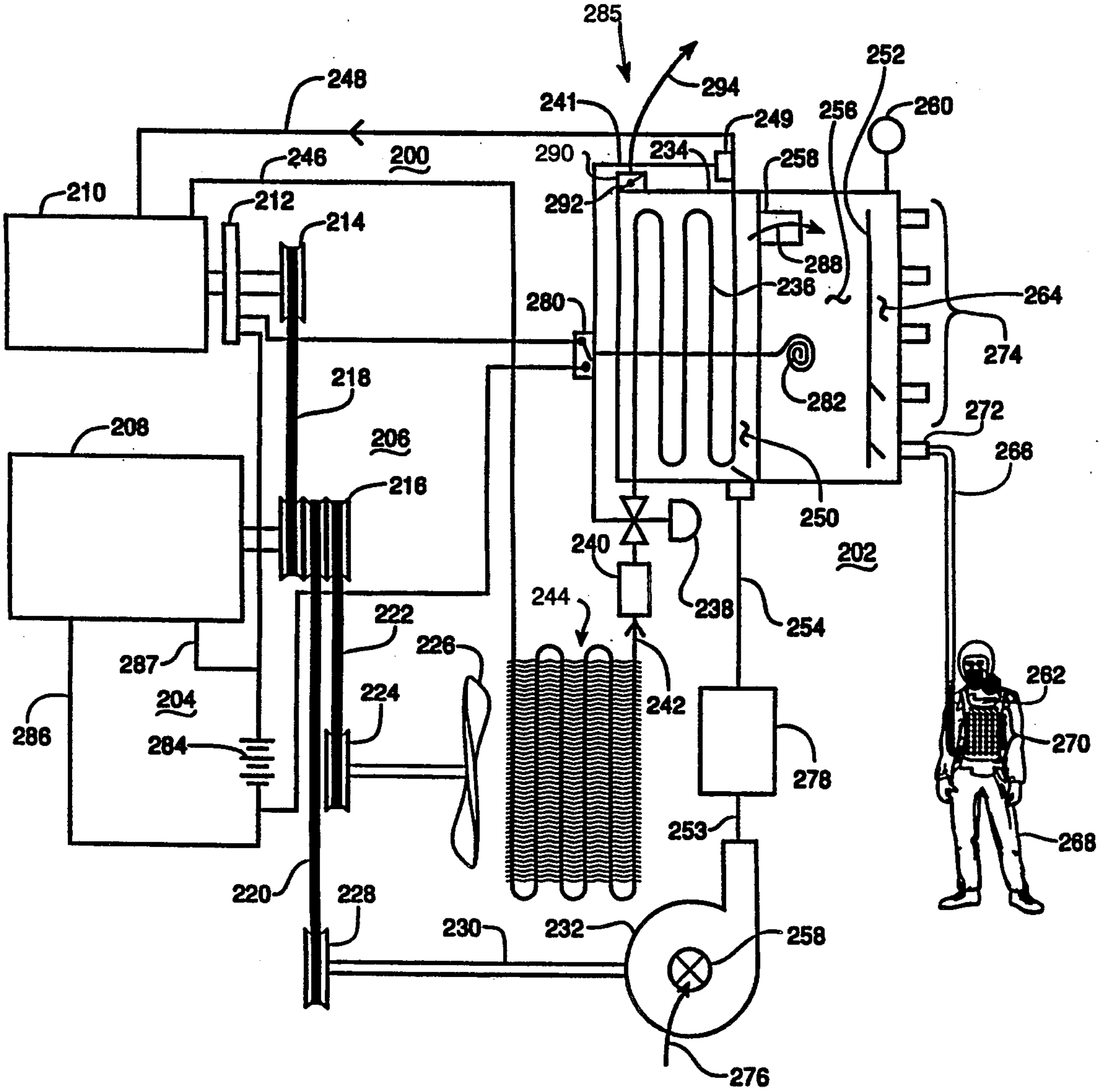
FIG. 2 shows a schematic diagram of a cooling system according to the present invention.
Figure 3:
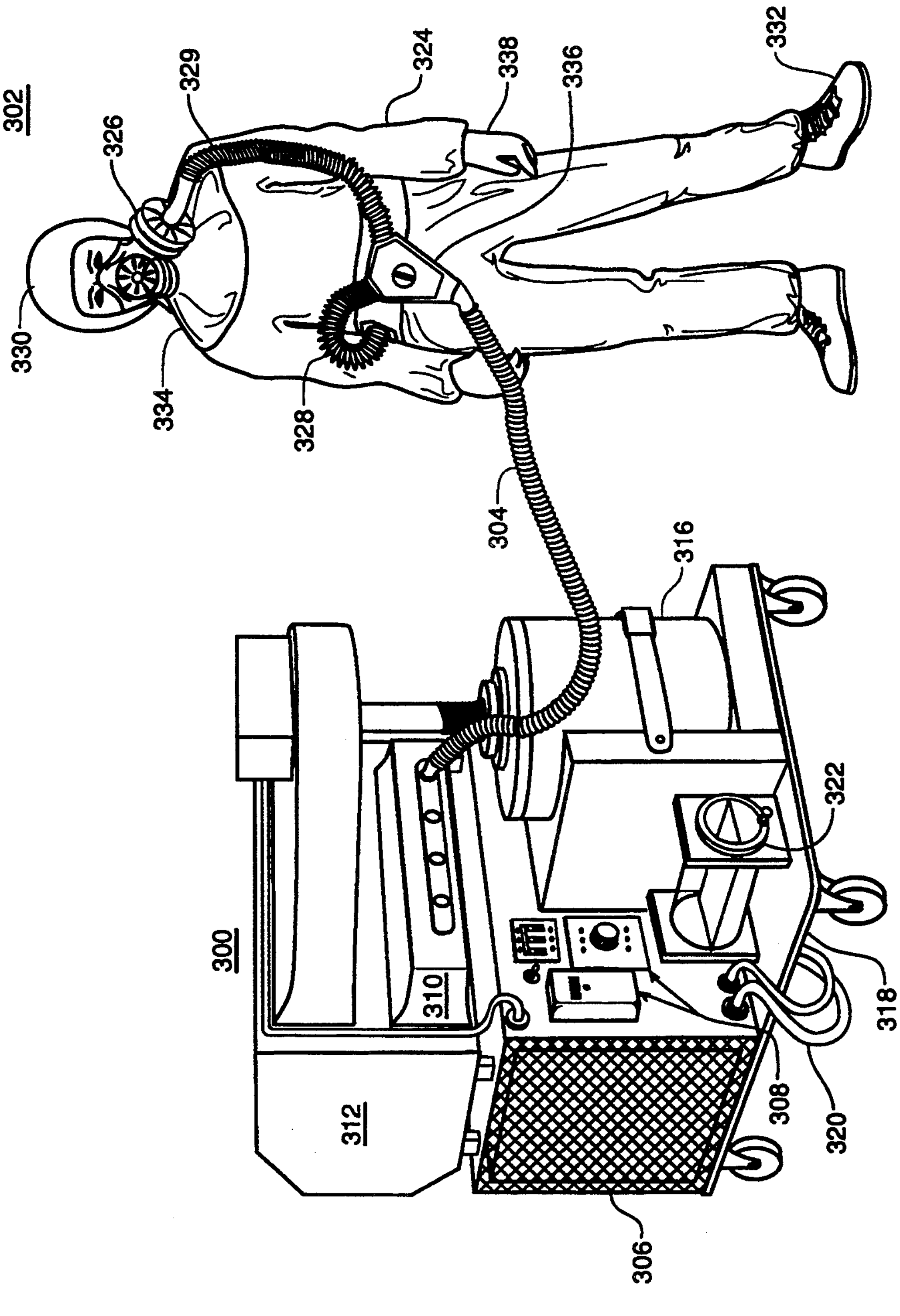
FIG. 3 shows additional details of the cooling apparatus in FIGS. 1 and 2.

FIG. 3 in the drawings shows one arrangement suitable for use at 100 in the FIG. 1 scene. In FIG. 3 a portable apparatus capable of supplying the needed quantity and quality of cooling air for up to five working persons is shown at 300 and a person utilizing this apparatus is shown at 302. The tether conduit by which treated air from the apparatus 300 is conveyed to the person 302 is indicated at 304 in FIG. 3. The FIG. 3 apparatus 300 is also shown to include a first housing 306 which contains a prime mover source of mechanical energy such as an internal combustion engine. The engine may be of the gasoline or diesel type or possibly comprise an electric motor. The compressor and condenser coils of a mechanical refrigeration apparatus and a condenser fan and other elements as are described in more detail in FIG. 2 of the drawings are also received in the housing 306.

Also shown in FIG. 3 is a treated air plenum 312 together with a manifold assembly 310 and an array of controls 308 for operating and regulating the cooling system.

Additionally shown in the FIG. 3 apparatus 300 is the air filter element 316 by which chemical warfare agents and other contaminants in the ambient atmosphere are removed from the air supplied to the person 302. Also, shown in FIG. 3 is the portable cart 318 on which the air treatment apparatus is mounted, the electrical cables 320 by which energy is supplied to an electric motor prime mover embodiment of the air treatment apparatus and a holding tank 322 for collecting condensate removed from the ambient air sent to the manifold 310.

The protected worker or person 302 is shown in the FIG. 3 drawing to be provided with a newer type of U.S. Military chemical protection suit 324 which includes the gloves 338 and the headgear assembly 330 and 334 and provides isolation of the protected person from a contaminated ambient environment. This newer type of protective clothing also includes contaminate impervious footware 332. An air divider assembly 336 by which clean, cooled and dried and pressurized air from the apparatus 300 is divided between facial and breathing uses, via the tubing member 329, and torso cooling functions via the tubing 328 is also shown in FIG. 3.

In practice it is found desirable for a twenty cubic feet per minute flow of air in the tether conduit 304 to be divided in the ratio of seventeen cubic feet per minute to the protected person's torso by way of the tubing 328 and the remaining three cubic feet per minute to be supplied by the tubing 329 and the mask assembly 326 to the facial area as cooling and breathing air. As is additionally explained below, the torso air is preferably distributed by an air vest member worn by the protected person 302.

The tether conduit 304 is shown in a shortened condition in FIG. 3 for drawing convenience purposes; it may actually be of considerable length, lengths up to 10 feet having been found to be practical. The tubing 304 is preferably of one inch diameter for moderate lengths of the tether with tubing of larger sizes being useful for longer length tethers as is known in the fluid and gas flow art.

A schematic diagram of apparatus suitable for use as the FIG. 3 source 300 of clean, temperature regulated and pressurized air is shown in FIG. 2 of the drawings. Quantitative details regarding a preferred arrangement of this apparatus are also disclosed in Table 1 located at the end of this specification. The FIG. 2. apparatus includes a combination of four energy communication circuits which are combined to provide an open loop source of temperature regulated and pressurized air for use in FIG. 1 efforts. The FIG. 2 apparatus includes a closed cycle refrigerant circuit, which is generally indicated by the number 200, an open loop air circuit, which is generally indicated by the number 202, a mechanical energy circuit 206, and an electrical control circuit generally indicated by the number 204.

In the mechanical energy circuit 206 in FIG. 2, a prime mover source of mechanical energy such as an electric motor or an internal combustion engine 208 (e.g. a gasoline or diesel engine) is provided with a pulley 216 which may be of the vee-belt variety. The compressor vee belt 218 is received on the pulley 216, along with the belt 220 to the centrifugal blower pulley 228, and the belt 222 to the fan pulley 224. All of these belts are mechanically driven by the preferred gasoline engine at 208 and the pulley 216 received thereon. The compressor pulley 214 is received on the input shaft of refrigerant compressor 210 and provides mechanical energization of the compressor 210 by way of an electrically operated slip clutch 212. In a similar manner, the belt 222 and the pulley 224 provide mechanical energization for the fan 226, this energization being most practically made to be continuous in nature so long as the engine 208 is running. The belt 220 and the pulley 228 also provide continuous rotation by way of the shaft 230 for the elevated pressure centrifugal blower 232.

The ambient air circuit 202 in FIG. 2 includes the centrifugal blower 232 and the pressurized air lines 253 and 254 which convey air to the enclosure 234 surrounding the evaporator coil 236 and thence to the cooled air plenum 256 and the cooled air supply manifold 264. A predetermined fixed temperature, preferably a temperature between fifty and fifty-five degrees Fahrenheit is maintained in the cooled air plenum 256 by way of the closed loop electrical control circuit 204 which includes the electrical switch 280 that is operated by a thermostatic sensing bulb 282. Upon an increase in the temperature of the air in the plenum 256 above the selected temperature, the switch 280 is closed to complete an electrical circuit from the battery 284 through the electrically operated clutch 212 to commence operation of the refrigerant compressor 210. Similarly, a falling of the air temperature in the plenum 256 below the selected regulation point causes opening of the switch 280 and disengagement of the clutch 212.

The battery 284 is maintained in a charged condition by an alternator-based charging system that is made integral with the engine 208 in the manner known in the engine art. The battery 284 may also be used for cranking or starting of the engine 208 with the electrical leads 286 and 287 being used to indicate the circuit for both cranking and battery charging uses.

If an electric motor is employed at 208 then the clutch 212 may be operated from a transformer/rectifier D.C. power supply as is known in the electrical art or alternately the clutch 212 may be of the type which is responsive to alternating current energization. Electric motor usage at 208 would also enable a physical combining of the motor at 208 and the compressor 210 into a single "hermetic" compressor arrangement as is known in the refrigeration art. In such instances, starting and stopping of the motor and compressor is used for temperature regulation and a separate motor or motors used for the blower 232 and fan 226. Portable combat area uses of the invention are however best accommodated with an internal combustion engine disposed at 208.

In the FIG. 2 refrigerant circuit 200, the compressor inlet line 248 is used to convey low-pressure refrigerant gas, gas which is preferably of the R-22 or chlorodifluoromethane type, from the evaporator coil 236 into the compressor 210. Mechanical energy from the engine 208 is used to raise the pressure and temperature of the gas emerging in the compressor output line 246. The elevated pressure and temperature gas in the line 246 is communicated to the finned condensing coil 244 where airflow induced by the fan 226 lowers the compressed gas temperature to approximately ambient temperature and thereby also transforms the gas into a liquid in the manner which is known in the refrigeration art.

The condensed refrigerant liquid is communicated along the line 242 to a receiver and dryer device 240 where small traces of moisture or other contaminants are removed from the refrigerant and excess quantities of the refrigerant are stored in liquid form. Liquid from the receiver/dryer device 240 is communicated to the thermal expansion valve 238 where an expansion transformation into a cold gas for application to the evaporator coil 236 is accomplished. The expansion from liquid to gas is controlled by a temperature feedback signal originating in a sensing bulb 249, and coupled from the evaporator coil output location of the bulb 249 to the expansion valve control apparatus along the path 241.

The enclosed spaced 250 which contains a double-layer evaporator coil 236 may be provided with a number of baffles and air flow directing elements as are known in the art. These baffles help achieve maximum heat transfer between the evaporator coil and the air flow 288 (which emerges from the enclosed space 250 by way of the aperture 258 into the plenum 256). The plenum 256 may also be provided with a baffle arrangement 252 in order to achieve desired air flow into each of the possible manifold output ports 272 and 274. A double layer evaporator coil is preferred at 236 in order to achieve large moisture removing capability in the FIG. 2 apparatus.

In the ambient air circuit 202 of the FIG. 2 apparatus air received into the inlet aperture 258 of the centrifugal blower 232 is indicated at 276. This air is pressurized up to a pressure in the range of eleven inches of water in the air line 253 by way of rotating the shaft 230 and the attached blade assembly in the blower 232. This eleven inch pressure is somewhat higher than might normally be expected in an air refrigeration apparatus in order that the needed volume and velocity of air be available to the filter 278 and then to each of the protected workers represented at 268 in FIG. 2. Pressures in this range are achieved in the blower 232 by way of a high blade velocity with this velocity being achieved in turn by a combination of high RPM at the shaft 230 and large diameter of the blower 232. Specific data is disclosed in Table 1 hereof. By way of comparison, this eleven inches of water operating pressure in the line 253 is almost twice the pressure normally used for the distribution of cooking and heating gas in the consumer supply lines of a municipal gas company and is about three times the pressure normally achieved in the squirrel cage blower of a residential heating and air conditioning system. This pressure is however somewhat less than the pressure often achieved in present day vacuum cleaner apparatus.

About six inches of this eleven inch operating pressure is used in forcing the contaminated air received from the ambient at 276 through the charcoal and other cleansing elements used in the air filter 278 in the FIG. 2 apparatus. The filtering element 278 may be a type M48 filter commonly used by the U.S. Army for providing life support air inside the crew compartment of a battle tank. Filters of this type are manufactured by the U.S. Army Armament R & D Command and are available under a U.S. government national stock number as is identified in table 1 herein.

Filters of this type are capable of operating in the range of 100 cubic feet per minute of output air and are moreover intended for operation with predetermined pressure drop and flow minimum values in order to assure removal of air contaminants. In the FIG. 2 apparatus these minimum air flow and pressure drop requirements for the filter 278 are met with the assistance of the air bleeding port apparatus 285 which allows for a flow 294 of shunt or bleed air as may be controlled by the valve 292 in order that minimum flow requirements of the filter 278 be met.

With a 100 cubic feet per minute flow through the filter 278 the pressure drop in the filter 278 is about six inches of water and the pressures realized in the line 254 and in the plenum 256 are in the range of five inches of water. This pressure is used to communicate the treated air by way of the tether tubing 266 to the protected worker indicated at 268 in FIG. 2. The pressure in the filter output line 254 and in the evaporator enclosure space 250 and the plenum 256 may be adjusted by way of the pressure gage 260 to meet the flow and pressure requirements of the filter 278 and other portions of the FIG. 2 apparatus.

The clean pressurized cooled and dried air in the manifold area 264 is conveyed to the protected person 268 by way of the single path tubing 266. As indicated in FIG. 3 this air is used for torso cooling and facial cooling plus breathing purposes in the CDWE clothing. The torso cooling portion of this use, to which most of the received air is devoted, is preferably accomplished with the aid of an air vest member which is indicated generally at 262 in FIG. 2. Vests of this type are also used by the U.S. Army for tank crew personnel cooling and one vest of this type is identified more completely in Table 1 hereof. Vests of these types are provided with a plurality of air venting holes which are generally indicated at 270 in FIG. 2 and by which the pressurized and velocity maintained air received along the tether tubing 266 is vented into the protective clothing worn by the person 268. From inside the protective Clothing the supplied air escapes through both inherent and predetermined location provided openings of the protective clothing into the ambient atmosphere. The outward flow through these openings precludes contaminant entry into the CDWE.

The FIG. 2 apparatus therefore can provide a fully portable source of cooled air that is capable of removing up to 6200 BTU of heat per hour per person from five or fewer persons. Notably this heat removal is accomplished by a twenty cubic feet per minute flow of moving dry air at velocities of 110 feet per second over the protected person's perspiring skin so that normal body cooling functions are preserved. Operation of the FIG. 2 apparatus may continue indefinitely so long as fuel is supplied to the engine 208 or energy to the corresponding electric motor. Moreover, this operation can be largely immune to the hostile nature of the chemical agent being removed in the FIG. 1 scene. The FIG. 2 apparatus may be mounted on a small cart or dolly and have a total weight in the 150 lb. range so that transportation to the scene of a cleanup activity is easily accomplished.

As is indicated in FIG. 1 herein, the present apparatus may be used in both a continuous cooling ongoing work activity mode and may also be used in the alternating work and rest period mode that was described in my earlier referred to previous patent application. FIGS. 3 and 4 in this earlier patent application provide useful test data indicating the benefit of even intermittently supplied cooling in a simulated clean-up test sequence and are useful in appreciating the present invention. The contents of my earlier Ser. No. 07/548,454 patent application are incorporated by reference herein.

In alternate arrangements of the present invention, it is of course, possible to supply a source of heat energy within or adjacent the plenum 256 in order that one or both of two additional useful results be achieved. According to one of these useful results, such heat could be used in instances where the FIG. 2 apparatus is employed in colder climates and additional warming of the FIG. 1 workers is desirable or alternately such heat may be used to elevate the temperature of air from the space 250 following an excessive cooling accomplished in order to remove greater amounts of moisture and provide an additional drying effect within the protective clothing of the protected persons. Such cooling and then reheating is often practiced in the air conditioning art as a means of obtaining extremely dry output air, air having a maximum degree of moisture absorbing capability.

The apparatus described herein may also be used for the cooling and contamination protection of electronic equipment and possibly aircraft simply by connecting such equipment, by way of a tether tubing conduit, to one of the manifold ports 274.

The described air cooling system therefore provides a low cost small size and light weight air supply system which may be used to enable human activity in a most hostile war time environment. In such uses, the equipment is of value in reducing heat stress and preventing heat casualties in a contaminated chemical warfare environment. The described apparatus will support personnel performing moderate or heavy work under contaminated conditions, such as may be incurred during rapid runway repair, ordinance loading, base maintenance and base security operations. The described apparatus may also be useful for peace-time endeavors in the cleanup of a toxic treatment facility or a contaminated nuclear facility or also for fire fighting and underground miner rescue operations including such operations performed where normal energy sources are unavailable.

TABLE 1

| Specifications, Numbers relate to FIG. 2 | |
|---|---|
| Cooling capacity of disclosed embodiment | 6200 BTU/Hr for each of 5 users at 105° F. ambient & 60° F. output, 31,000 BTU/hr total. |
| Supplied air volume | 20 cubic ft/min/person (100 cubic ft/min total) |
| Size | 40 × 24 × 40 (in., LWH) |
| Weight | 150 lbs |
| Output air temperature | 50° F. to 60° F. adjustable |
| Prime Mover, 208 | Gasoline or diesel engine 10HP or electric motor 8 HP, |
| Refrigerant | R-22 chlorodifluoromethane |
| Thermal expansion value, 238 | Parker N-2FW, $\frac{3}{4}$-2 tons, −40 to +40° F., 60-175 PSI |
| Compressor, 210 | York automotive Model 206 1000 RPM |
| Condenser, 244 | 14" H × 20" L × $1\frac{1}{4}$" W 5/16" Dia & 13/32" Dia |
| Condenser inlet temperature | 150° F. at 105° F. ambient |
| Condenser outlet temperature | 117° F. at 105° F. ambient |
| Condenser fan 226 | 1/15 HP, 16" 4 blade, 1100 RPM |
| Evaporator, 236 | H coil $22\frac{1}{8}$" H × $30\frac{1}{2}$" W 2.1 tons, double layer |
| Receiver-dryer 240 | Frigette $2\frac{1}{2}$" Dia × $8\frac{1}{4}$" L 5/16" Dia connector |
| Centrifugal blower 232 | Vacuum type by Ametek Inc, 6 27/34" dia, 2 stage centrifugal, 17,800 RPM |
| Temperature Control 280, 282 | Honeywell −30° F. to 9° F. |
| Filter 278 | U.S. ARMY M48, NSN 4240-01-161-3710 gas particulate NBC, 100 CFM charcoal plus hepa treated filter |
| Air vest 262 | Open weave fabric 17SCFM NSN 84 15-01-217-5634 |
| Tether tubing 266 | flexible, insulated, 10 ft 1" ID NSN 1660-00-795-1485 |

I claim:

1. Open loop portable personal cooling apparatus for work and cleanup assistance in a chemical warfare agent contaminated elevated temperature and elevated humidity ambient environment comprising the combination of:

chemical protection suit means for isolating a wearer from ambient environment;

a prime mover source of rotational mechanical energy;

refrigeration apparatus including an evaporator coil and a mechanical compressor member and a condenser fan member energized from said prime mover energy source;

electrically energized clutch means including a mechanical torque transmitting clutch member for intermittently communicating rotational mechanical energy between said prime mover source of mechanical energy and said mechanical compressor member;

air communication means including a centrifugal blower member of eleven inches of water column pressure capability energized from said prime mover mechanical energy source for communicating a predetermined volume of cooled and dried ambient air from said evaporator coil portion of said refrigeration apparatus into said chemical protection suit means;

said predetermined volume of cooled and dried air being distributed in a perspiration evaporating moving predetermined pattern of distribution over torso and facial portions of said wearer; and pressurized air cleansing means disposed between said centrifugal blower member and said evaporator coil portion of said refrigeration apparatus for removing ambient air contaminating chemical warfare agent from an output stream flow from said centrifugal blower member.

2. The cooling apparatus of claim 1 further including an air vest member disposed over the upper torso portion of a protected person.

3. The cooling apparatus of claim 1 wherein said prime mover source of rotational mechanical energy comprises one of an electric motor and an internal combustion engine.

4. The cooling apparatus of claim 1 further including a manifold member disposed in air path communication with said evaporator coil and wherein said manifold member communicates with a plurality of one-way air flow distribution tethers for a corresponding plurality of protected persons.

5. The cooling apparatus of claim 1 wherein said predetermined volume of cooled and dried air comprises a volume of twenty cubic feet per minute for each protected person connected with said apparatus.

6. The cooling apparatus of claim 1 wherein said air cleansing means comprises a gas sorption charcoal filter.

7. The cooling apparatus of claim 6 wherein said filter is a one hundred cubic feet per minute type M-48 U.S. Army filter of national stock number 4240-01-161-3710.

8. Open loop portable environment generating apparatus for chemical warfare cleanup assistance in a chemical contaminated ambient air environment having extreme temperature and humidity limitations, said apparatus comprising:

a chemical protection suit adapted to be worn by a wearer seeking isolation from the ambient air environment, said protection suit including an air vest member disposable in an upper torso body portion and interior region of said chemical protection suit, and a facial mask means for delivering breathable air to an upper interior facial region of said chemical protection suit;

a ten horsepower gasoline engine comprising a source of rotational mechanical energy having battery start and battery charging capabilities;

closed cycle fluorinated hydrocarbon gas refrigeration apparatus including a compressed gas condenser member and a mechanical compressor member energized from said gasoline engine through an electric clutch and also including a condenser cooling fan member mechanically energized from said gasoline engine;

ambient air communicated centrifugal blower means also mechanically energized from said gasoline engine for generating one hundred cubic feet per minute and eleven inches of water pressurized flow of contaminated ambient air;

air cleaning means, having a charcoal sorption element therein and a connection between an output port of said centrifugal blower means and an evaporator coil air cooling portion of said refrigeration apparatus, for removing said chemical warfare contamination and other impurities from said pressurized ambient air flow, said air cleaning means having a six inches of water column pressure drop and a one hundred cubic feet per minute flow rate characteristic;

air communication means including a five inches of water pressurized air plenum and air manifold members and a single path hollow tubing tether member of one inch nominal diameter connected with said pressurized manifold member for distributing a twenty cubic feet per minute flow of cleansed, cooled and dried ambient air therefrom to said chemical protection suit;

said air communication means also including manually controllable air bypassing means for establishing an air cleansing means flow rate maintaining and pressure maintaining shunt flow of cleansed and cooled ambient air return to the ambient air environment; and airflow divider means, located adjacent said chemical protection suit, for dividing said twenty cubic feet per minute airflow into a pair of perspiration evaporating air flows, having volumetric flow ratios of seventeen and three cubic feet per minute respectively at said air vest member and said facial mask means of said chemical protection suit.

9. Open loop portable personal cooling apparatus for work and cleanup assistance in a chemical warfare agent contaminated elevated temperature and elevated humidity ambient environment comprising the combination of:

a chemical protection suit adapted to be worn by a wearer seeking isolation from said ambient environment;

a prime mover source of rotational mechanical energy;

refrigeration apparatus including a mechanical compressor member and a condenser fan member each energized from said prime mover energy source;

electrically energized clutch means including a mechanical torque transmitting clutch member for intermittently communicating rotational mechanical energy between said prime mover source of mechanical energy and said mechanical compressor member;

said refrigeration apparatus including an evaporator coil, and closed cycle fluorinated hydrocarbon refrigeration gas system, and a cooled air temperature responsive mechanical energization control system inclusive of said electrically energized clutch means;

air communication means including a centrifugal blower member, of eleven inches of water column pressure capability, energized from said prime mover mechanical energy source for communicating a predetermined volume of cooled and dried ambient air from said evaporator coil portion of said refrigeration apparatus into said chemical protection suit;

said predetermined volume of cooled and dried air being distributed in a perspiration evaporating moving predetermined pattern of distribution into torso and facial portions of said chemical protection suit; and pressurized air cleansing means disposed between said centrifugal blower member and said evaporator coil portion of said refrigeration apparatus for removing said ambient air contaminating chemical warfare agent from an output stream flow from said centrifugal blower member.

* * * * *